United States Patent
Shao et al.

(10) Patent No.: US 11,756,678 B1
(45) Date of Patent: Sep. 12, 2023

(54) METHODS AND SYSTEMS FOR SCHEDULING VACCINES IN SMART CITIES BASED ON INTERNET OF THINGS (IOT)

(71) Applicant: CHENGDU QINCHUAN IOT TECHNOLOGY CO., LTD., Sichuan (CN)

(72) Inventors: Zehua Shao, Chengdu (CN); Yaqiang Quan, Chengdu (CN); Yongzeng Liang, Chengdu (CN); Haitang Xiang, Chengdu (CN); Zhihui Wen, Chengdu (CN)

(73) Assignee: CHENGDU QINCHUAN IOT TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 17/661,275

(22) Filed: Apr. 28, 2022

(30) Foreign Application Priority Data

Apr. 6, 2022 (CN) .......................... 202210353121.9

(51) Int. Cl.
  *G16H 40/20* (2018.01)
  *G16H 50/80* (2018.01)
  (Continued)

(52) U.S. Cl.
  CPC ......... *G16H 40/20* (2018.01); *G06Q 10/1095* (2013.01); *G16H 50/80* (2018.01); *G16Y 10/60* (2020.01)

(58) Field of Classification Search
  CPC .............................. G16H 40/20; G16H 50/80
  See application file for complete search history.

(56) References Cited

U.S. PATENT DOCUMENTS

| | | | |
|---|---|---|---|
| 11,232,870 B1* | 1/2022 | Shaashua | G06N 20/20 |
| 2008/0091471 A1* | 4/2008 | Michon | G16B 40/20 |
| | | | 705/3 |

(Continued)

FOREIGN PATENT DOCUMENTS

| | | |
|---|---|---|
| CN | 107578613 A | 1/2018 |
| CN | 109146264 A | 1/2019 |

(Continued)

OTHER PUBLICATIONS

Shao, Zehua, Exploration and Research on the Structure of Internet of Things, Internet of Things Technologies Reliable Transmission, 2015, 10 pages.

(Continued)

*Primary Examiner* — Rajesh Khattar
*Assistant Examiner* — Steven G. S. Sanghera
(74) *Attorney, Agent, or Firm* — METIS IP LLC

(57) ABSTRACT

The present disclosure provides a method and system for scheduling vaccines in a smart city based on the Internet of Things (IoT), which is executed by a vaccine management platform. The method includes obtaining a service scope corresponding to each vaccination point in a preset area, obtaining information related to vaccine service within the service scope, the information related to the vaccine service including vaccination information, information of target persons to be vaccinated, and a time type of each preset time point, determining a prediction result based on the information related to the vaccine service within the service scope, the prediction result including a number of possible to-be-vaccinated persons at the each vaccination point at the each preset time point, and determining an allocation scheme based on the prediction result.

8 Claims, 5 Drawing Sheets

(51) Int. Cl.
*G06Q 10/1093* (2023.01)
*G16Y 10/60* (2020.01)

(56) References Cited

U.S. PATENT DOCUMENTS

| | | | | |
|---|---|---|---|---|
| 2008/0183547 | A1* | 7/2008 | Halaby | G16H 40/20 |
| | | | | 705/7.21 |
| 2009/0018871 | A1* | 1/2009 | Essig | G06Q 30/0236 |
| | | | | 705/26.1 |
| 2016/0232494 | A1* | 8/2016 | Katou | G16H 10/60 |
| 2017/0206557 | A1* | 7/2017 | Abrol | G06Q 50/01 |
| 2021/0319890 | A1* | 10/2021 | Ahmed | G16H 40/67 |
| 2022/0291011 | A1* | 9/2022 | Selina | G01C 21/3679 |

FOREIGN PATENT DOCUMENTS

| | | | |
|---|---|---|---|
| CN | 109934439 | A | 6/2019 |
| CN | 110503320 | A | 11/2019 |
| CN | 111444429 | A | 7/2020 |
| CN | 111680813 | A | 9/2020 |
| CN | 112633681 | A | 4/2021 |
| CN | 112866358 | A | 5/2021 |
| CN | 113192647 | A | 7/2021 |
| CN | 113724847 | A | 11/2021 |
| CN | 109146264 | B * | 4/2022 ....... G06Q 10/06315 |

OTHER PUBLICATIONS

Shao, Zehua, The Internet of Things sense the world beyond the world, China Renmin University Press, 2017, 30 pages.
Shao, Zehua, Smart City Architecture, Internet of Things Technologies Intelligent Processing and Application, 2016, 7 pages.
White Paper on Urban Brain Development, Smart City Standard Working Group of National Beacon Commission, 2022, 59 pages.
Guo, Shicheng et al., Construction and Application of the Integrated Immunization Program Information Management System Based on a Cloud Platform in Jiangxi Province, Chinese Journal of Vaccines and Immunization, 28(1): 110-114, 2022.
Zhuang, Luruo et al, Exploration of Big Data Technology for Infectious Disease Epidemic Prevention and Control Strategies, China Rural Health, 2022, 4 pages.
Huang, Dacang, Monitoring Hand, Foot and Mouth Disease Based on Search Engine Query Data, Chinese Master's Theses Full-text Database Information Science and Technology, 2015, 56 pages.
First Office Action in Chinese Application No. 202210353121.9 dated May 20, 2022, 26 pages.
Notification to Grant Patent Right for Invention in Chinese Application No. 202210353121.9 dated Jun. 4, 2022, 7 pages.

* cited by examiner

METHODS AND SYSTEMS FOR SCHEDULING VACCINES IN SMART CITIES BASED ON INTERNET OF THINGS (IOT)

CROSS-REFERENCE TO RELATED APPLICATIONS

This application claims priority to Chinese Patent Application No. 202210353121.9 filed on Apr. 6, 2022, the contents of which are hereby incorporated by reference to its entirety.

TECHNICAL FIELD

The present disclosure relates to the field of information management, and in particular, to methods and systems for scheduling vaccines in smart cities based on Internet of Things (IoT).

BACKGROUND

Vaccination is closely related to people's livelihood. Especially in the case of a large-scale epidemic, there exists a situation where a large number of persons come to vaccinate at hospitals, community service points, and other vaccination points in the city. It is a challenge to reasonably arrange a number of vaccines and vaccination time for to-be-vaccinated persons at each vaccination point to avoid crowding of vaccination population.

The IoT is an important part of a new generation of information technology and an extended and expanded network based on the Internet, which combines various information sensing devices with the network to form a huge network to realize an interconnection of persons, machines, and things at any time and anywhere. The IoT provides a technical basis for cities with dense populations and large demands of vaccination. It is of great significance to design a management system for scheduling vaccines based on the IoT. Therefore, it is desirable to provide methods for efficiently scheduling vaccines and reasonably arranging vaccination in combination with the IoT technology.

SUMMARY

One aspect of some embodiments of the present disclosure provides a method for scheduling vaccines in a smart city based on IoT. The method may be executed by a vaccine management platform. The method may include obtaining a service scope corresponding to each vaccination point in a preset area. The method may also include obtaining information related to vaccine service within the service scope, and the information related to the vaccine service may include vaccination information, information of target persons to be vaccinated, and a time type of each preset time point. The method may also include determining a prediction result based on the information related to the vaccine service within the service scope, and the prediction result may include a number of possible to-be-vaccinated persons at the each vaccination point at the each preset time point. The method may further include determining an allocation scheme for the vaccines based on the prediction result.

One aspect of some embodiments of the present disclosure provides a system for scheduling vaccines of in a smart city based on IoT. The system may include a vaccine management platform, a vaccine service platform, and a user platform. The vaccine management platform may be configured to obtain a service scope corresponding to each vaccination point in a preset area, obtain information related to vaccine service within the service scope, the information related to the vaccine service including vaccination information, information of target persons to be vaccinated, and a time type of each preset time point, determine a prediction result based on the information related to the vaccine service within the service scope, the prediction result including a number of possible to-be-vaccinated persons at the each vaccination point at the each preset time point, and determine an allocation scheme for the vaccines based on the prediction result.

Another aspect of some embodiments of the present disclosure provides a non-transitory computer readable storage medium storing a set of instructions. The set of instructions may be executed by at least one processor. The at least one processor may be configured to perform a method for scheduling vaccines in a smart city based on IoT.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
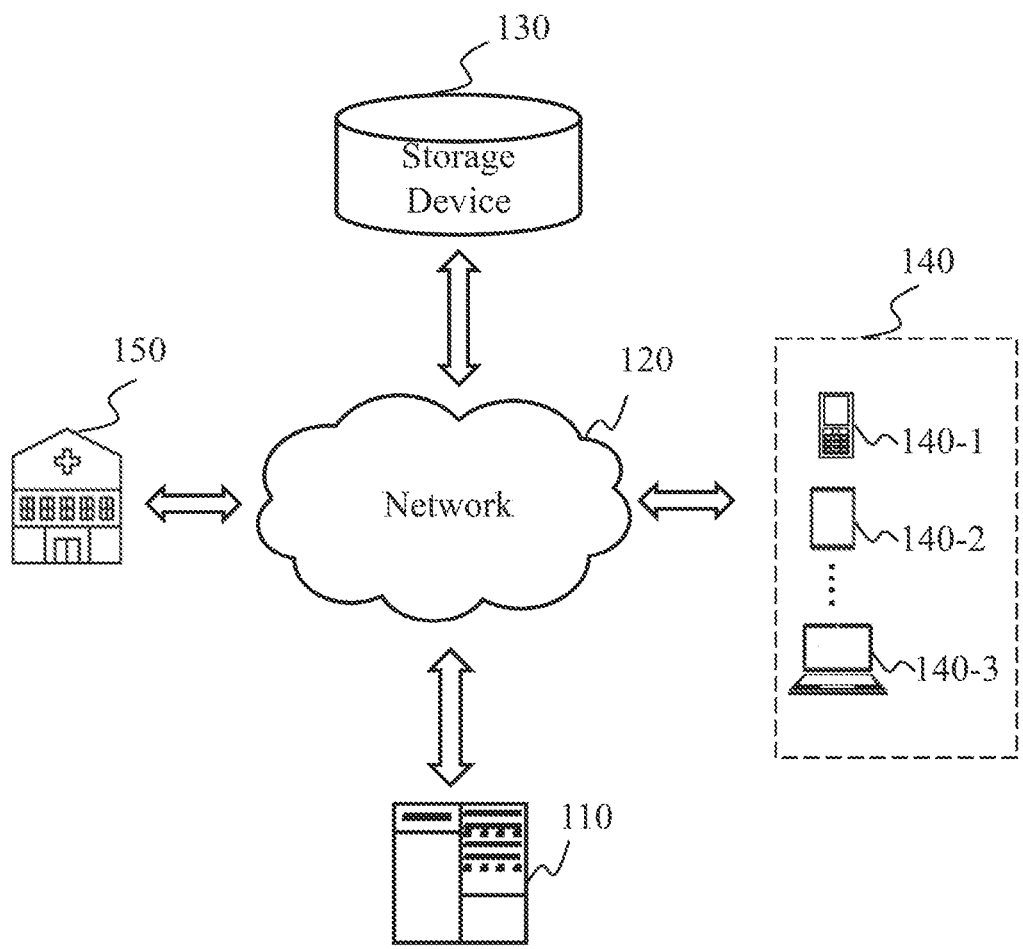
FIG. 1 is a schematic diagram illustrating an exemplary application scenario of a system for scheduling vaccines in a smart city according to some embodiments of the present disclosure.

In the following detailed description, numerous specific details are set forth by way of examples in order to provide a thorough understanding of the relevant disclosure. Obviously, drawings described below are only some examples or embodiments of the present disclosure. Those skilled in the art, without further creative efforts, may apply the present disclosure to other similar scenarios according to these drawings. It should be understood that the purposes of these illustrated embodiments are only provided to those skilled in the art to practice the application, and not intended to limit the scope of the present disclosure. Unless obviously obtained from the context or the context illustrates otherwise, the same numeral in the drawings refers to the same structure or operation.

It will be understood that the terms "system," "device," "unit," and/or "module" used herein are one method to distinguish different components, elements, parts, sections, or assemblies of different levels. However, the terms may be displaced by another expression if they achieve the same purpose.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

FIG. 1 is a schematic diagram illustrating an exemplary application scenario of a system for scheduling vaccines in a smart city according to some embodiments of the present disclosure. As shown in FIG. 1, in some embodiments, an application scenario 100 may include a processing device 110, a network 120, a storage device 130, a user terminal 140, and a vaccination point terminal 150.

In some embodiments, the processing device 110, the storage device 130, the user terminal 140, and/or the vaccination point terminal 150 may connect and/or communicate with each other via the network 120 (e.g., wireless connection, wired connection, or any combination thereof). As shown in FIG. 1, the processing device 110 may be connected to the storage device 130 via the network 120. As another example, the user terminal 140 may be connected to the processing device 110 and the storage device 130 via the network 120.

The processing device 110 may be used to process information and/or data related to the application scenario 100, such as prediction results, allocation schemes of vaccines, etc. The processing device 110 may process data, information, and/or processed results obtained from other devices or components of the system, and execute program instructions based on the data, the information, and/or the processed results to perform one or more functions described in the present disclosure. In some embodiments, the processing device 110 may be configured to manage and maintain a vaccine management platform.

The network 120 may connect various components of the application scenario 100 and/or connect the application scenario 100 to external resources. The network 120 may enable communication between components and with other parts outside the application scenario 100 to facilitate exchange of data and/or information. The network 120 may include a local area network (LAN), a wide area network (WAN), an Internet, or the like, or any combination thereof.

The storage device 130 may be configured to store data and/or instructions. In some embodiments, the storage device 130 may store data and/or instructions executed by the processing device 110 to implement an exemplary method described in the present disclosure. In some embodiments, the storage device 130 may be connected to the network 120 to communicate with one or more components of the application scenario 100 (e.g., the processing device 110, the user terminal 140).

The user terminal 140 may include one or more terminal devices or software. In some embodiments, the user terminal 140 may include a mobile phone 140-1, a tablet 140-2, a laptop 140-3, or the like. In some embodiments, users may view information and/or enter data and/or instructions through the user terminal 140. For example, the users may input an instruction for querying vaccination information through the user terminal 140. For another example, the users may view vaccination information through the user terminal 140.

The vaccination point terminal 150 may be a computing device, which is arranged in a vaccinating point for vaccinating persons. In some embodiments, the vaccination point terminal 150 may include, but is not limited to, a computing device at a vaccination point such as a hospital, a community service point, etc. In some embodiments, the users may receive service at the vaccination point, the service including but not limited to vaccination, consultation, etc. In some embodiments, the vaccination point terminal 150 may communicate with one or more components (e.g., the processing device 110, the user terminal 140) of the application scenario 100 via the network 120.

It should be noted that the application scenario is only provided for illustrative purposes and is not intended to limit the scope of the present disclosure. For those skilled in the art, various modifications or changes may be made based on the description of the present disclosure. For example, the application scenario may implement similar or different functions on other devices. However, changes and modifications do not depart from the scope of the present disclosure.

The IoT system is an information processing system including at least one of a management platform, a service platform, and a user platform. The management platform may realize overall planning and coordination of connection and cooperation between various functional platforms (e.g., the service platform and the user platform). The management platform may provide perception management and control management for operation of the IoT system by gathering information of the operation of the IoT system. The service platform may connect the management platform to the user platform, which plays functions of sensing information service communication and controlling information service communication. The user platform may be a functional platform for obtaining user perception information and generating control information.

The processing of information in the IoT system may be divided into a processing flow of the users' perception information and a processing flow of the control information. The control information may be information generated based on the user perception information. In some embodiments, the control information may include user demand control information, and the user perception information may include information of a user query. Processing of the information of user query may include obtaining information by the user platform, the information related to search, browsing, uploading, and feedback carried out by the users on the user platform, and transmitting the information from the management platform to the user platform through the service platform. The user demand control information may be distributed from the user platform to the management platform through the service platform, so as to provide demand services for corresponding users.

In some embodiments, when the IoT system is applied to city management, it may be referred to as an IoT system in a smart city.

Figure 2:
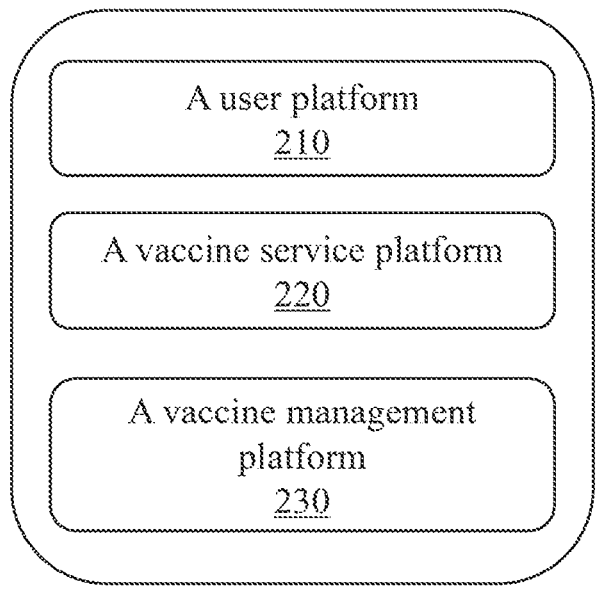
FIG. 2 is a schematic diagram illustrating an exemplary system for scheduling vaccines in a smart city according to some embodiments of the present disclosure.

FIG. 2 is a schematic diagram illustrating an exemplary system for scheduling vaccines in a smart city according to some embodiments of the present disclosure. As shown in FIG. 2, in some embodiments, a system 200 for scheduling vaccines in a smart city may be implemented based on the IoT system. In some embodiments, the system 200 may include a user platform 210, a vaccine service platform 220, and a vaccine management platform 230. In some embodiments, the system 200 may be a part of the processing device 110 or implemented by the processing device 110.

In some embodiments, the system 200 may be applied to a variety of scenarios of scheduling vaccines. In some embodiments, the system 200 may respectively obtain vaccination information under various scenarios to determine scheduling vaccine strategies under various scenarios. In some embodiments, the system 200 may obtain scheduling vaccine strategies of a whole region (such as a city) based on the obtained vaccination information under various scenarios.

Various scenarios of scheduling vaccines may include scheduling of a number of vaccines, scheduling of vaccination time, prediction of scheduling vaccines, etc. It should be noted that the above scenarios are only examples and do not limit specific application scenarios of the system 200 for scheduling vaccines in a smart city. Those skilled in the art may apply the system 200 for scheduling vaccines in a smart city to any other suitable scenarios on the basis of the contents described in some embodiments of the present disclosure.

In some embodiments, the system 200 may be applied to the scheduling of the number of vaccines. When applied to the scheduling of the number of vaccines, the vaccine management platform 230 may obtain information of each vaccination point in a certain area (such as a city, a district in a city, etc.) and population in the area. The vaccination points may include pre-set hospitals, temporary community service vaccination points, etc. The vaccine management platform 230 may set a service scope for the each vaccination point, for example, setting a service radius of the vaccination point. The larger the service radius is, the more allocated vaccines are. The vaccine management platform 230 may determine strategies or instructions related to scheduling of the number of vaccines according to the service scope of the vaccination point and the population within the service scope, such as instructions for expanding or reducing the service radius of the vaccination point. The vaccine management platform 230 may upload a scheduling strategy of the number of vaccines to the vaccine service platform 220, and the vaccine service platform 220 may upload the scheduling strategy to the user platform 210 to feedback to the user.

In some embodiments, when the system 200 is applied to the scheduling of the number of vaccines, the user platform 210 may collect information of user query for a vaccination point. For example, in a certain time period, a vaccination point may be queried by the user through the user terminal device. The number of queries for the vaccination point is more, indicating that popularity of the vaccination point is higher and possible persons who may be vaccinated at the vaccination point is more. The user platform 210 may send the collected query information of the vaccination points as the user demand control information to the vaccine service platform 220. The vaccine service platform 220 may further send the query information to the vaccine management platform 230, and the vaccine management platform 230 may determine strategies or instructions (such as allocation of additional vaccines) related to the scheduling of the number of vaccines based on statistical data of the collected query information. The vaccine management platform 230 may upload the strategies related to the scheduling of the number of vaccines to the vaccine service platform 220, and the vaccine service platform 220 may upload the strategies to the user platform 210 to feedback to the user.

In some embodiments, the system 200 may be applied to the scheduling of vaccination time. When applied to the scheduling of vaccination time, the vaccine management platform 230 may obtain population information within the service scope of the vaccination point, which may include population distribution of all age groups, such as the population under the age of 18, between the age of 18 and 50, and over the age of 50. The population information may also include professional information, such as whether the person is in employment, industry, workplace, etc. The vaccine management platform 230 may determine strategies or instructions related to the scheduling of vaccination time based on the population information. For example, arranging persons under the age of 18 and over the age of 50 to vaccinate on weekdays (such as Monday to Friday), and arranging persons between the ages of 18 and 50 to vaccinate on weekends (such as Saturday or Sunday). The vaccine management platform 230 may upload the scheduling strategies of vaccination time to the vaccine service platform 220, and the vaccine service platform 220 may upload the scheduling strategies to the user platform 210 to feedback to the user.

In some embodiments, the system 200 may be applied to a prediction of scheduling vaccines. When applied to the prediction of scheduling vaccine, the vaccine management platform 230 may collect data related to the prediction of scheduling vaccines. The data related to the prediction of scheduling vaccines may include epidemic situation information in the region (such as a number of confirmed cases, a number of suspected confirmed cases, a number of severe cases, a number of asymptomatic cases, etc.), a number of to-be-vaccinated and non-vaccinated persons in the region, a number of queries for the vaccination point, etc. The vaccine management platform 230 may determine strategies or instructions (e.g., predicting a number of vaccinators at the each vaccination point in a next period of time for allocating the number of vaccines) related to the prediction of scheduling vaccines by processing the above information. The vaccine management platform 230 may upload prediction results of scheduling vaccines to the vaccine service platform 220, and the vaccine service platform 220 may upload the prediction results to the user platform 210 to feedback to the user.

In some embodiments, the system 200 may be composed of a plurality of subsystems for scheduling vaccines in a smart city, and each subsystem may be applied to one scenario. The system 200 may comprehensively manage and process data obtained and output by each subsystem, so as to obtain relevant strategies or instructions for assisting scheduling vaccines in the smart city.

For example, the system 200 may include a subsystem applied to scheduling of a number of vaccines, a subsystem applied to scheduling of vaccine time, and a subsystem applied to a prediction of scheduling vaccines. The system 200 may serve as a superior system of each subsystem.

The following will take the system 200 to manage each subsystem and obtain corresponding data based on the subsystem to determine a strategy of scheduling vaccines in a smart city as an example:

The system 200 may obtain an allocation of a number of vaccines at the each vaccination point based on a subsystem for scheduling a number of vaccines, obtain an allocation of vaccination time at the each vaccination point based on a subsystem for scheduling vaccination time, and obtain prediction data of the allocation of the number of vaccines at the each vaccination point at a time period in the future based on a subsystem for predicting scheduling vaccines.

When obtaining the above data, the system 200 may separately set multiple management platforms corresponding to each subsystem for data collection.

For example, the system 200 may set a city infrastructure management sub platform. The city infrastructure management sub platform may determine data of preset vaccination service scope of the each vaccination point based on initial regional planning of the each vaccination point in the region (such as hospitals and community service vaccination points), and upload the data to the vaccine management platform 230. The vaccine management platform 230 may adjust a service scope of the each vaccination point based on a combination of the data of preset vaccination service scope of the each vaccination point and the number of queries for the each vaccination point on the user platform, and further adjust an arrangement of the number of vaccines of the each vaccination point.

For another example, the system 200 may set a city population information management sub platform. The city population information management sub platform may conduct statistical processing based on the population information in the region, such as statistics on the population distribution of all ages, occupation, work information, and other data in the region. The city population information management sub platform may also upload the statistical data to the vaccine management platform 230. The vaccine management platform 230 may determine an arrangement of vaccination time based on the above data, for example, arranging retirees and children to vaccinate on weekdays, and arranging students and office workers to vaccinate on weekends.

For another example, the system 200 may set a government epidemic information management sub platform. The government epidemic information management sub platform may upload the epidemic situation data such as the number of confirmed cases, the number of suspected cases, the number of severe cases, and the number of asymptomatic cases in the region to the vaccine management platform 230. Based on the epidemic situation data, and in combination with the number of queries for the each vaccination point on the user platform and vaccination results at the each vaccination point, the vaccine management platform 230 may predict a number of persons to be vaccinated at a time period in the future and determine an allocation scheme for vaccines at a time period in the future. The vaccine management platform 230 may upload the prediction results of scheduling vaccines to the vaccine service platform 220, and the vaccine service platform 220 may upload the prediction results to the user platform 210 to feedback to the user.

For those skilled in the art, after understanding the principle of the system, it is possible to move the system to any other suitable scene without departing from this principle.

The following will take the system 200 applied to a prediction scenario of scheduling vaccines as an example:

The user platform 210 may refer to a user-dominated platform, including a platform for obtaining user needs and feeding information back to the users. In some embodiments, the user platform may be configured to query for vaccination information by inputting instructions through the user terminal. In some embodiments, the user platform may be configured to display an arrangement of vaccines through a display terminal.

The vaccine service platform 220 may refer to a platform that conveys the user needs and control information. The vaccine service platform 220 may connect the user platform 210 and the vaccine management platform 230. In some embodiments, the vaccine service platform 220 may query for the vaccination information by obtaining the query instruction sent by the user through the user platform, and feed the vaccination information back to the user.

The vaccine management platform 230 may refer to a platform for scheduling vaccines. In some embodiments, the vaccine management platform 230 may belong to a management platform. The vaccine management platform 230 may be configured to obtain a service scope corresponding to the each vaccination point in a preset area and information related to the vaccine service within the service scope. The information related to the vaccine service may include vaccination information, information of target persons to be vaccinated, and a time type of each preset time point.

In some embodiments, the vaccine management platform 230 may be configured to determine a prediction result based on the information related to the vaccine service within the service scope, and the prediction result may include a number of possible to-be-vaccinated persons at each preset time point.

In some embodiments, the vaccine management platform 230 may be configured to determine a prediction result by inputting the information related to the vaccine service within the service scope into a prediction model.

In some embodiments, an input of the prediction model may also include a change feature of popularity at the each vaccination point. The change feature of popularity at the each vaccination point may be dynamically changed based on change factors, the change factors may at least include an epidemic situation and an spread degree at the each vaccination point. The change feature of popularity may be obtained through a feature model, which is used to process the epidemic situation information at the each vaccination point and the number of queries on the user platform to determine the change feature of popularity.

In some embodiments, the vaccine management platform 230 may be configured to determine an allocation scheme for vaccines based on the prediction results.

In some embodiments, the vaccine management platform 230 may be configured to determine the number of vaccines allocated to the each vaccination point and the vaccination time based on the prediction results to generate the allocation scheme for the each vaccination point. A vaccination arrangement may be generated through the vaccine management platform based on the allocation scheme.

In some embodiments, the vaccine management platform 230 may be configured to send the vaccination arrangement through the vaccine service platform 220 in response to the user query for vaccination information at the each vaccination point through the user platform 210. The vaccination arrangement may be sent to the user platform 210 through the vaccine service platform 220 for displaying the vaccination information for a user.

It should be noted that the above descriptions of the system and its components are intended to be convenient, and one or more embodiments of the present disclosure may not be limited to the scope of the disclosure. It may be understood that after understanding the principle of the system, those skilled in the art may arbitrarily combine the components or form a subsystem to connect with other components without departing from the principle. For example, the vaccine management platform and the vaccine service platform may be integrated into one component. For another example, each component may share a storage device, and each component may also have respective storage devices. Those variations and modifications may be within the scope of the protection of one or more embodiments of the disclosure.

Figure 3:
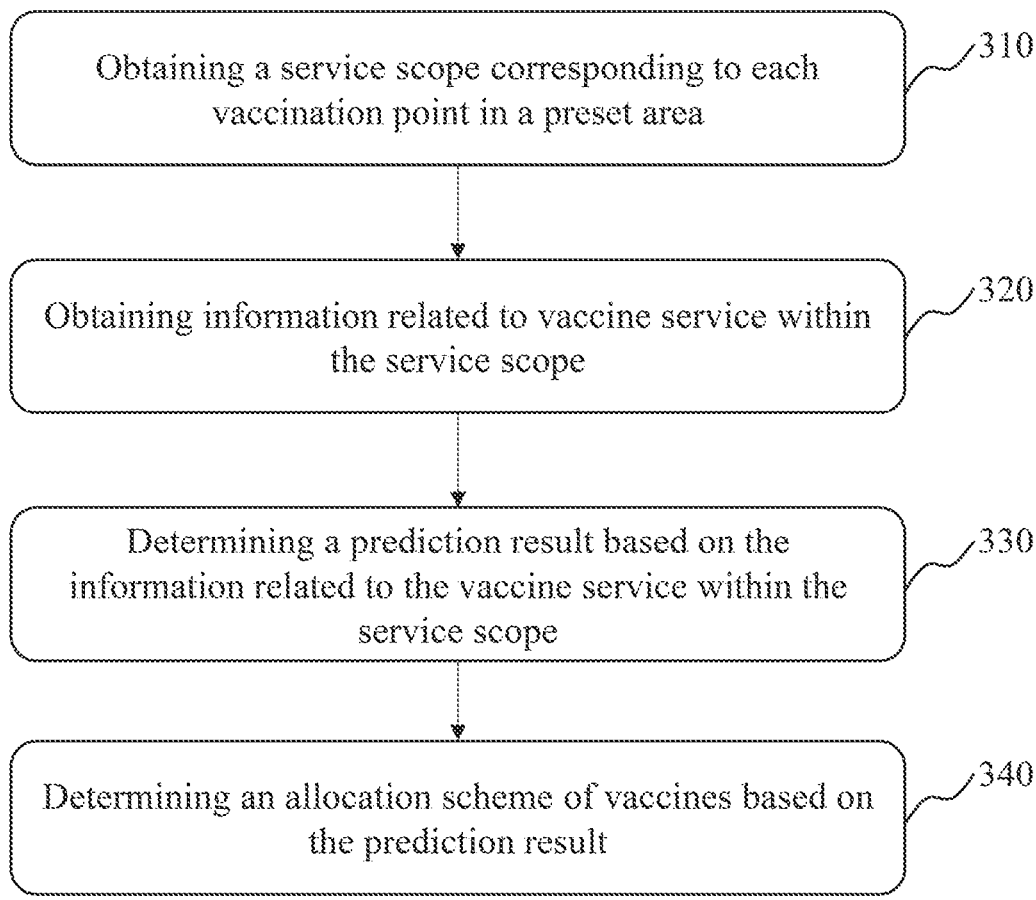
FIG. 3 is a flowchart illustrating an exemplary process of a method for scheduling vaccines in a smart city according to some embodiments of the present disclosure.

FIG. 3 is a flowchart illustrating an exemplary process of a method for scheduling vaccines in a smart city according to some embodiments of the present disclosure. As shown in FIG. 3, the process 300 may include the following steps. In some embodiments, the process 300 may be executed by the vaccine management platform 230.

In step 310, the vaccine management platform 230 may obtain a service scope corresponding to each vaccination point in a preset area.

In some embodiments, the vaccine management platform 230 may determine the preset area in a variety of ways. In some embodiments, the vaccine management platform 230 may determine a plurality of preset areas based on administrative division. For example, the vaccine management platform may determine multiple preset areas such as Chengdu, Deyang, and Leshan based on the administrative division of Sichuan Province. In some embodiments, the vaccine management platform may determine a preset area based on user input. For example, if the user input is within 10 kilometers from the user current position, the vaccine management platform may determine an area within 10 kilometers from the user current position as a preset area.

It is understandable that the vaccine management platform may also determine a larger or smaller preset area based on different needs and/or tasks. For example, the vaccine management platform may determine one or more provinces as a preset area. For example, the vaccine management platform may determine one or more streets as a preset area.

Vaccination points may refer to sites where persons are vaccinated. For example, the vaccination points may be hospitals or temporary medical service points. In some embodiments, the vaccination points may be preset. In some embodiments, the vaccination points may include preset hospitals and/or temporary community service vaccination sites in the preset area.

In some embodiments, the vaccine management platform may obtain relevant information of the vaccination points through national and/or local government service websites. For example, the vaccine management platform may obtain the number and location of the vaccination points through the Chengdu government service website.

The service scope may refer to a geographical and spatial distribution scope of the persons vaccinated at the vaccination point. For example, a service scope of a street vaccination point may be an administrative jurisdiction region of the street.

In some embodiments, the vaccine management platform may obtain the service scope corresponding to the each vaccination point in the preset area. In some embodiments, the vaccine management platform may determine the service scope corresponding to the each vaccination point based on historical data of the each vaccination point in the preset area. For example, the vaccine management platform may determine a distribution scope as a service scope of a vaccination point based on the geographical and spatial distribution scope of the population vaccinated at the vaccination point in the past year.

In some embodiments, the vaccine management platform may determine the service scope corresponding to the each vaccination point in the preset area based on preset rules. The preset rules may be preset artificially. In some embodiments, the user may flexibly set the preset rules based on different needs and/or tasks. In some embodiments, the preset rules may include preset radius, administrative jurisdictions, etc. The following will take the preset rules being preset radius as an example.

In some embodiments, the vaccine management platform may modify the preset radius based on statistical information. The statistical information may include but is not limited to population information, the number of vaccines information, etc. In some embodiments, the vaccine management platform may count the number of persons vaccinated at two vaccination points at the historical period when the two vaccination points are adjacent in the service scope, and modify the preset radius of each vaccination point based on proportion of the number of persons vaccinated at two vaccination points.

Exemplary, a service scope of vaccination point A and a service scope of vaccination point B may be adjacent, and an initial preset radius of the vaccination point A and the vaccination point B may be 2 km. Based on the statistical information, the vaccine management platform may obtain the number of persons vaccinated at the vaccination point A and the vaccination point B in January being 10000, respectively, the number of persons vaccinated at the vaccination point A in February being 15000, and the number of persons vaccinated at the vaccination point B being 5000, that is, the number of persons vaccinated at the vaccination point A is increased and the number of persons vaccinated at the vaccination point B is decreased. Based on the proportion of the population, the vaccine management platform may modify the preset radius of the vaccination point A in March to 3 km and modify the preset radius of the vaccination point B to 1 km.

In some embodiments, the vaccine management platform may also modify the preset radius based on the change feature of popularity for the each vaccination point. More descriptions regarding the change feature of popularity for the each vaccination point may be found elsewhere in the present disclosure, for example, FIG. 5 and its relevant descriptions thereof.

In some embodiments, the vaccine management platform may first obtain the change feature of popularity at two adjacent vaccination points in the service scope, then calculate vector distances (e.g., Euclidean distance) respectively based on a reference feature of the vaccination points. The farther the vector distance is, indicating that the popularity is lower, and the preset radius may be smaller. The vaccine management platform may finally correct two preset radius based on proportion of the results of calculated vector distance. The reference feature may refer to a pre-set feature that represents the highest popularity, for example, the reference feature may be used to indicate a maximum number of online reservation services from the users within the preset time in the service scope or its surrounding service scope.

Exemplary, the reference feature may be preset as a feature vector C, feature vectors of the popularity of vaccination points A and B may be vector A and vector B respectively, the vectors A and B may be calculated with the reference vector C respectively to obtain vector distances D1 and D2 respectively. If a spatial distance between the vaccination points A and B is 1000 m, the vector distance D1 is 2, and the vector distance D2 is 2, indicating the popularity of both the vaccination points A and B is the same, that is, a radius of the service scope of the vaccination points A and B is the same (e.g., 500 m). If the popularity of the vaccination points A and B is different, for example, the vector distance D1 is 2 and the vector distance D2 is 3, the radius of the service scope of the vaccination point A is 3/5 times of the spatial distance, i.e. 600 m, the radius of the service scope of the vaccination point B is 2/5 times of the space distance, i.e. 400 m. That is, the vector distance D1 is smaller than the vector distance D2, indicating the popularity of the vaccination point A is higher than the vaccination point B, so the radius of the service scope of the vaccination point A is set larger.

In some embodiments, the vaccine management platform may also modify the preset radius in other ways. For example, a trained machine learning model based on historical data may be used for modifying the preset radius.

In step 320, the vaccine management platform 230 may obtain information related to the vaccine service within the service scope.

The information related to the vaccine service may refer to information associated with the vaccine service, for example, information related to vaccines, information related to to-be-vaccinated persons, etc. In some embodiments, the information related to the vaccine service may include vaccination information, information of target persons to be vaccinated, and a time type of each preset time point.

The vaccination information may refer to information related to vaccinated or non-vaccinated persons. For example, the number of vaccinated and non-vaccinated persons, occupation, and age of vaccinated and non-vaccinated persons, etc. In some embodiments, the vaccination information may include the number of un-vaccinated persons of all ages.

The information of target persons to be vaccinated may refer to information related to non-vaccinated persons. In some embodiments, the information of target persons to be vaccinated may include population and population mobility information of each age group. For example, a number of persons aged at 20, where and when the persons came from here, etc.

The preset time point may refer to a time point set in advance. For example, Saturday, 9 a.m., etc. In some embodiments, the vaccine management platform may determine a preset time point based on the user input through the user terminal.

The time type of the each preset time point may refer to a type that the preset time point belongs to. In some embodiments, the vaccine management platform may divide the time type into a weekend type and a weekday type. In some embodiments, the vaccine management platform may determine Monday, Tuesday, Wednesday, Thursday, and Friday as the weekday type. In some embodiments, the vaccine management platform may determine Saturday and Sunday as the weekend type.

In some embodiments, the vaccine management platform may obtain information related to the vaccine service within the service scope. In some embodiments, the vaccine management platform may obtain the information related to the vaccine service within the service scope based on the user input through the user terminal. For example, the information input by the user through the user terminal may include vaccinated or non-vaccinated information. The vaccine management platform may count the number of vaccinated and non-vaccinated persons to obtain the vaccination information within the service scope.

In step 330, the vaccine management platform 230 may determine a prediction result based on the information related to the vaccine service within the service scope.

The prediction result may refer to the number of persons to be vaccinated at the each vaccination site in the future. In some embodiments, the prediction result may include the number of possible to-be-vaccinated persons at the each vaccination point at the each preset time point. For example, the number of possible to-be-vaccinated persons at the vaccination point A on Saturday may be 200 and the number of possible to-be-vaccinated persons at the vaccination point A on Sunday may be 250.

In some embodiments, the vaccine management platform may determine the prediction result based on the information related to the vaccine service within the service scope. In some embodiments, the vaccine management platform may determine the prediction result based on comparison the information related to the vaccine service within the service scope with information related to historical vaccine service within the service scope. For example, the vaccine management platform may determine that the number of possible to-be-vaccinated persons at the vaccination point A on Saturday is always twice than that on Monday based on the information of historical vaccine services, so the vaccine management platform may determine that the number of vaccination at the vaccination point A on Saturday of this week is 200 if the number of vaccination at the vaccination point A on Monday of this week is 100.

In some embodiments, the vaccine management platform may also determine the prediction result by a prediction model. More description regarding determining prediction results through a prediction model may be found elsewhere in the present disclosure, for example, FIG. 5 and its relevant description thereof.

In step 340, the vaccine management platform may determine an allocation scheme for the vaccines based on the prediction result.

The allocation scheme for the vaccines may refer to an arrangement of allocating vaccines to the vaccination points. In some embodiments, the allocation scheme may include an arrangement of the number of vaccines and vaccination time at the each vaccination point based on the number of possible to-be-vaccinated persons. For example, the allocation scheme may include arranging 50 vaccines for the vaccination point A on Monday.

In some embodiments, the vaccine management platform may determine the allocation scheme for the vaccines based on the prediction result. For example, if the predicted result is that the number of possible to-be-vaccinated persons at the vaccination point A on Saturday is 200, the vaccine management platform may determine that the allocation scheme for the vaccines is that the vaccination point A needs 400 vaccines on Saturday.

Figure 4:
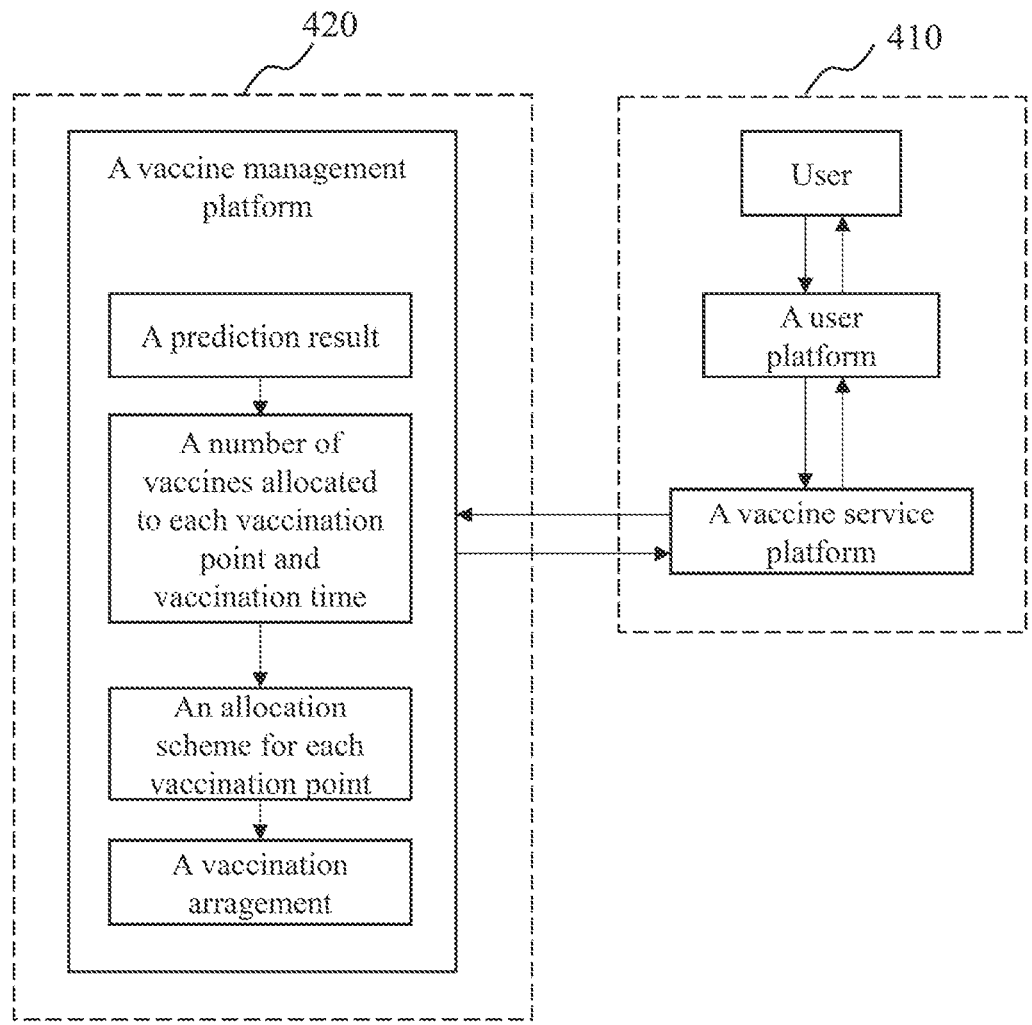
FIG. 4 is a schematic diagram illustrating an exemplary process for querying vaccination information according to some embodiments of the present disclosure.

More descriptions regarding determining the allocation scheme based on the prediction results may be found elsewhere in the present disclosure, for example, FIG. 4 and its relevant descriptions thereof.

Some embodiments of the present disclosure may obtain the service scope corresponding to the each vaccination point in the preset area through the vaccine management platform, and further obtain information related to the vaccine service within the service scope, which may finely and accurately determine information related to the vaccine service. The accuracy of vaccine allocation may be improved by determining the prediction result based on the information related to the vaccine service and further determining the allocation scheme for the vaccines.

FIG. 4 is a schematic diagram illustrating an exemplary process for querying vaccination information according to some embodiments of the present disclosure. As shown in FIG. 4, process 400 may include the following steps. In some embodiments, the process 400 may be executed by the vaccine management platform.

In step 410, in response to user query for the vaccination information at the each vaccination point through the user platform, the vaccine management platform may send the vaccination arrangement through the vaccine service platform.

The vaccination arrangement may refer to a plan of vaccination for the each vaccination point at the each preset time point. For example, the vaccination point A will have 200 vaccines to vaccinate on Saturday and the vaccination point A will have 300 vaccines to vaccinate on Sunday. In some embodiments, the vaccination arrangement may be sent to the user platform through the vaccine service platform for displaying the vaccination information to the user. Feedback methods may include but be not limited to SMS reminder, email reminder, etc.

In some embodiments, the vaccine management platform may send the vaccination arrangement through the vaccine service platform in response to the user query for the vaccination information at the each vaccination point through the user platform. For example, as shown in FIG. 4, the user may input information and/or view information through the user platform, and the user platform may communicate with the vaccine service platform in response to the information and/or instructions input by the user. If the user queries for the vaccination information at the each vaccination point through the user platform, the vaccine management platform may send the vaccination arrangement to the user platform through the vaccine service platform. Thus, the user may view the vaccination arrangement indicating the vaccination information.

In step 420, the vaccine management platform may determine the number of vaccines allocated to the each vaccination point and the vaccination time to generate the allocation scheme at the each vaccination point based on the prediction result, and generate the vaccination arrangement based on the allocation scheme. In some embodiments, relevant information of the vaccination arrangement may be fed back to users through the vaccine service platform and the user platform.

In some embodiments, the vaccine management platform may determine the number of vaccines allocated to the each vaccination point and the vaccination time based on the prediction results, so as to generate the allocation scheme for the each vaccination point. For example, the vaccine management platform may determine, based on the predicted result that the number of possible to-be-vaccinated persons is 200 on Saturday, that the number of vaccines to be allocated at the vaccination point A is 200 and vaccination time is on Saturday, and generate an allocation scheme for the vaccination point A that the vaccination point A needs 200 vaccines on Saturday.

In some embodiments, the vaccine management platform may arrange the vaccinated persons according to different nature of persons based on the prediction result. The different nature of persons may include but not limited to retirees, children, students, office workers, etc. For example, the vaccine management platform may arrange the vaccination time for retirees on Monday and office workers on Saturday and Sunday based on the prediction result that the number of possible to-be-vaccinated persons including retirees and office workers at the vaccination point A on Saturday is 200.

In some embodiments, the vaccine management platform may generate the vaccination arrangement based on the allocation scheme. In some embodiments, the vaccine management platform may generate vaccination arrangement through user input based on the allocation scheme. For example, the user may enter their time that they only have free time on Saturday and Sunday through the user platform, and the vaccine management platform may arrange for the user to vaccinate at the vaccination point on Saturday or Sunday.

Some embodiments of the present disclosure may obtain the vaccination arrangement through the vaccine service platform in communication with the vaccine management platform, so as to feed back the user query, which can improve accuracy and timeliness of the vaccination arrangement. At the same time, the allocation scheme is generated based on the prediction result and the vaccination arrangement is further generated, which can improve accuracy of the vaccination arrangement.

It should be noted that the above descriptions of the process are only intended to be convenient, and one or more embodiments of the present disclosure may not be limited to the scope of the disclosure. For those skilled in the art, various modifications and changes may be made to the process under the guidance of the present disclosure. However, those variations and modifications may be within the scope of the protection of one or more embodiments of the present disclosure.

Figure 5:
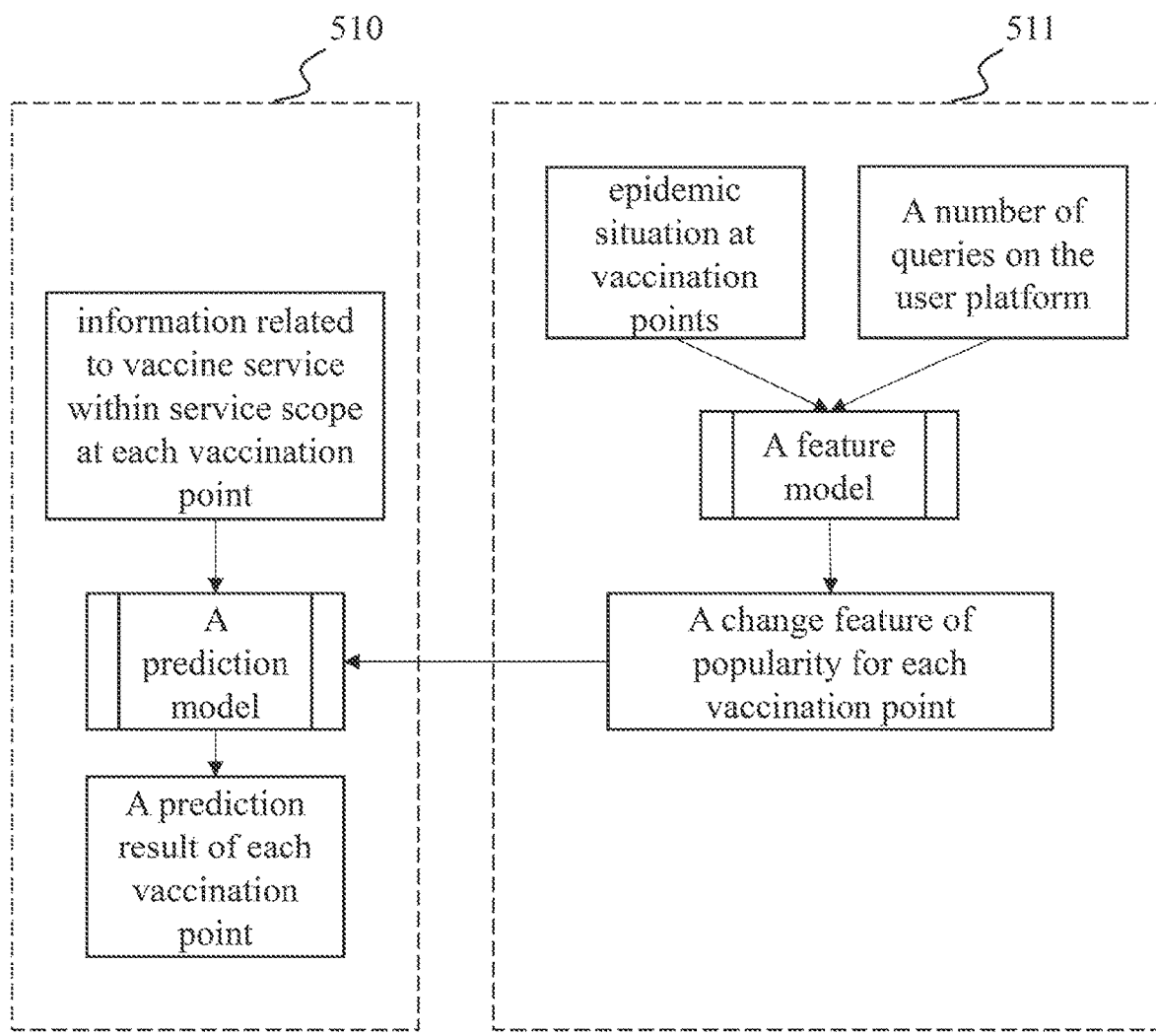
FIG. 5 is a schematic diagram illustrating an exemplary process for determining a prediction result by a prediction model according to some embodiments of the present disclosure.

FIG. 5 is a schematic diagram illustrating an exemplary process for determining a prediction result by a prediction model according to some embodiments of the present disclosure. As shown in FIG. 5, the process 500 may include the following steps. In some embodiments, the process 500 may be executed by the vaccine management platform.

In step 510, the vaccine management platform may determine a prediction result by inputting the information related to the vaccine service within the service scope into a prediction model.

The prediction model may refer to a model for determining the prediction result. The prediction model may be a trained machine learning model. In some embodiments, the prediction model may be a deep neural network model. In some embodiments, the prediction model may include other models, such as a cyclic neural network model, a convolutional neural network, or other custom model structure, or the like, or any combination thereof.

In some embodiments, the vaccine management platform may determine the prediction result by inputting the information related to the vaccine service within the service scope into the prediction model.

In some embodiments, an input of the prediction model may also include information related to the vaccination points. For example, geographical location of the vaccination points, a maximum number of vaccines that may be vaccinated at the vaccination points in a day, etc.

In some embodiments, the input of the prediction model may also include the change feature of popularity at the each vaccination point.

The change feature of popularity at the each vaccination point may refer to a feature obtained based on a change of values representing attention of the each vaccination point over a period of time. The values representing attention of the each vaccination point may refer to a probability value of vaccination at the each vaccination point and/or the each vaccination point used as target vaccination points by persons.

In some embodiments, the change feature of popularity at the each vaccination point may be affected by other factors. Other factors may include but are not limited to price, population, supply and demand, etc. For example, if a vaccine price at vaccination point A rises, the change feature of popularity may decline. For another example, most persons within the service scope at the vaccination point A have been vaccinated, and the change feature of popularity may decline.

In some embodiments, the change feature of popularity at the each vaccination point may be dynamically changed based on change factors, the change factors may at least include an epidemic situation and an spread degree at the each vaccination point.

The change factors may refer to factors that affect popularity for the vaccination points. In some embodiments, the change factors may include at least the epidemic situation and the spread degree at the each vaccination point.

The epidemic situation at the each vaccination point may refer to an epidemic development (e.g., the number of diagnosed cases, the number of suspected diagnosed cases, the number of severe cases, and the number of asymptomatic cases, etc.) within the service scope at the vaccination point. In some embodiments, the vaccine management platform may obtain the epidemic situation at the each vaccination point through the government epidemic information management sub platform.

The spread degree may refer to a degree to which a vaccination point is known in the persons. In some embodiments, the spread degree may be expressed by numbers, words, etc. For example, the spread degree at the vaccination point A may be 80%.

In some embodiments, the vaccine management platform may determine the spread degree based on the user query. The user query may refer to a query of the user for vaccination information at the each vaccination point on the user platform. The number of user queries may be referred to as information of the number of queries on the user platform. In some embodiments, the vaccine management platform may obtain the number of the user queries through the user platform, and the number of queries is determined as the spread degree at the vaccination point. For example, based on the user platform, the vaccine management platform may obtain the number of users accounts for querying vaccination point A being 400 and the number of persons within the service scope at the vaccination point A being 1000, and preliminarily determine the spread degree at the vaccination point A being 40%.

In some embodiments, the vaccine management platform may train the prediction model to learn parameters of the prediction model using a plurality of labeled training samples through a variety of methods (e.g., a gradient descent method). A training may be finished and a trained prediction model may be obtained until meeting preset conditions.

The training sample may be information related to historical vaccine service within the service scope. The training label may be a corresponding historical prediction result and a label of the training sample may be obtained by manual labeling. In some embodiments, the prediction model may be trained in another device or module.

In some embodiments, a step 510 may include a sub-step 511 for obtaining the change feature of popularity.

In step 511, the change feature of popularity may be obtained by the feature model.

The feature model may refer to a model for determining the change feature of popularity. The feature model may be a trained machine learning model. In some embodiments, the feature model may include a cyclic neural network model, a convolutional neural network, other custom model structure, or the like, or any combination thereof.

In some embodiments, the feature model may determine the change feature of popularity through processing the epidemic situation information at the each vaccination point and the number of queries at the vaccination point on the user platform. For example, as shown in step 511 of FIG. 5, the feature model may determine the change feature of popularity at the vaccination point through processing the epidemic situation information at the vaccination point and the number of queries at the vaccination point on the user platform.

In some embodiments, the feature model may be obtained based on joint training of multiple models. For example, the feature model may be obtained by joint training two initial feature models and a similarity model.

In some embodiments, when jointly training the feature model, the training samples of the two initial feature models may be obtained based on historical sample data at the same vaccination point. In some embodiments, at least one of two inputs of the two initial feature models may be different. For example, one or both of the epidemic situation information at the same vaccination point and the number of queries at the same vaccination point input by the two initial feature models may be different.

In some embodiments, an input of the similarity model may be outputs of the two initial feature models, and an output of the similarity model may be a similarity of the vaccination results at the vaccination point. The vaccination results may refer to the number of vaccinations in a preset time period. In some embodiments, the vaccination results may include the number of vaccinations in each age group, the number of vaccinations in areas at different distances from the vaccination point, etc. Understandably, the vaccination results may be different at different times. In some embodiments, the vaccine management platform may determine the vaccination results at different times based on the epidemic situation information at the same vaccination point at different times and the number of queries at the same vaccination point.

In some embodiments, the two initial feature models may be the same models, and parameters of the two initial feature models may be shared. In some embodiments, the two initial feature models may be named as a first initial feature model and a second initial feature model, respectively.

The first initial feature model and the second initial feature model may be trained machine learning models. In some embodiments, the first initial feature model and the second initial feature model may both be LSTM models. In some embodiments, the first initial feature model and the second initial feature model may include other models, such as a cyclic neural network model, a convolutional neural network, other customized model structures, or the like, or any combination thereof.

In some embodiments, the first initial feature model and the second initial feature model may determine different change feature of popularity through processing different epidemic situation information and different number of queries. For example, the first initial feature model may determine a first change feature of popularity and a first vaccination result at the same time through processing the first epidemic situation information and the first number of queries at the vaccination point A. The second initial feature model may determine a second change feature of popularity and a second vaccination result at the same time through processing the second epidemic situation information and the number of second queries at the vaccination point A.

The similarity model may be a trained machine learning model. In some embodiments, the similarity model may be a deep neural network model. In some embodiments, the similarity model may include other models, such as a cyclic neural network model, a convolutional neural network, other customized model structures, or the like, or any combination thereof.

In some embodiments, the similarity model may determine a similarity of vaccination results through processing the first vaccination result and the second vaccination result.

In some embodiments of the present disclosure, in some cases, the parameters of the feature model obtained through the above training method may be conducive to solving the problem that it is difficult to obtain labels when training the feature model alone and also enable the feature model to obtain relevant parameters that may better reflect the change features of popularity.

In some embodiments of the present disclosure, the prediction results may be determined by the prediction model, which can reduce the participation of labor and reduce the labor cost. Further, the prediction results may be accurately generated by inputting the change features of popularity into the prediction model.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for scheduling vaccines in a smart city based on Internet of Things (IoT), wherein the method is implemented based on a system for scheduling the vaccines in the smart city based on the IoT, and the system for scheduling the vaccines in the smart city based on the IoT includes a user platform, a vaccine service platform, and a city vaccine management platform;

the method being executed by a processor of the city vaccine management platform, the method comprising:
obtaining a service scope corresponding to each vaccination point in a preset area;
generating information related to vaccine service within the service scope by collecting information via network, wherein the information is input by a user from a user terminal, and the information related to the vaccine service includes vaccination information, information of target persons to be vaccinated, and a time type of each preset time point;
determining a change feature of popularity by processing an epidemic situation information at the each vaccination point and a number of queries on the user platform based on a feature model, wherein the feature model is a machine learning model, and the feature model is obtained through a training process, comprising:
  collecting a historical epidemic situation information and a historical number of queries at the each vaccination point from a vaccination point terminal;
  generating a plurality of groups of training samples and labels, wherein each group of training samples includes a first training data and a second training data, the first training data and the second training data are collected from a same vaccination point, the historical epidemic situation information or the historical number of queries of the first training data and the second training data are different, and a label of each group of training samples is a difference of vaccination results within a historical time period;
  inputting the plurality of groups of training samples into an initial feature model, wherein the initial feature model includes a first initial feature model, a second initial feature model, and an initial similarity model;
  for each group of the plurality of groups of training samples, extracting sample change features of popularity corresponding to the first training data and the second training data based on the first initial feature model and the second initial feature model;
  for each group of the plurality of groups of training samples, determining a first change feature of popularity and a first vaccination result based on extracted sample change features of popularity corresponding to the first training data, and determining a second change feature of popularity and a second vaccination result based on extracted sample change features of popularity corresponding to the second training data;
  for each group of the plurality of groups of training samples, outputting a predicted difference of vaccination result in the historical time period by determining a similarity of vaccination results through processing the first vaccination result and the second vaccination result based on the initial similarity model, thereby obtaining a plurality of predicted differences of vaccination results for the plurality of groups;
  generating a trained similarity model by updating parameters of the initial similarity model based on differences between the labels and the plurality of predicted differences of vaccination results; and
  generating a trained feature model by extracting parameters of any one of the first initial feature model and the second initial feature model and migrating the parameters of any one of the first initial feature model and the second initial feature model to the initial feature model;
determining a prediction result by inputting the information related to the vaccine service within the service scope and the change feature of popularity for the each vaccination point into a prediction model, the prediction result including a number of possible to-be-vaccinated persons at the each vaccination point at the each preset time point, wherein the prediction model is a machine learning model;
determining an allocation scheme for the vaccines based on the prediction result; and
transmitting the allocation scheme to the vaccination point terminal.

2. The method of claim 1, further comprising:
  in response to a user query for vaccination information at the each vaccination point through the user platform, sending a vaccination arrangement to the user platform through the vaccine service platform for displaying the vaccination information to a user.

3. The method of claim 1, wherein the change feature of popularity for the each vaccination point is dynamically changed based on change factors, the change factors at least including the epidemic situation and a spread degree at the each vaccination point.

4. The method of claim 1, wherein the determining an allocation scheme for the vaccines based on the prediction result includes:
  generating the allocation scheme for the each vaccination point by determining, based on the prediction result, a number of vaccines allocated to the each vaccination point and vaccination time; and
  generating a vaccination arrangement based on the allocation scheme.

5. A system for scheduling vaccines of in a smart city based on Internet of Things (IoT), the system including a city vaccine management platform, a vaccine service platform, and a user platform, wherein the city vaccine management platform is configured to perform operations comprising:
  obtaining a service scope corresponding to each vaccination point in a preset area;
  generating information related to vaccine service within the service scope by collecting information via network, wherein the information is input by a user from a user terminal, and the information related to the vaccine service includes vaccination information, information of target persons to be vaccinated, and a time type of each preset time point;
  determining a change feature of popularity by processing an epidemic situation information at the each vaccination point and a number of queries on the user platform based on a feature model, wherein the feature model is a machine learning model, and the feature model is obtained through a training process, comprising:
    collecting a historical epidemic situation information and a historical number of queries at the each vaccination point from a vaccination inoculation point terminal;
    generating a plurality of groups of training samples and labels, wherein each group of training samples includes a first training data and a second training data, the first training data and the second training data are collected from a same vaccination point, the historical epidemic situation information or the historical number of queries of the first training data and the second training data are different, and a label of each group of training samples is a difference of vaccination results within a historical time period;
    inputting the plurality of groups of training samples into an initial feature model, wherein the initial feature model includes a first initial feature model, a second initial feature model, and an initial similarity model;
    for each group of the plurality of groups of training samples, extracting sample change features of popularity corresponding to the first training data and the second training data based on the first initial feature model and the second initial feature model;
    for each group of the plurality of groups of training samples, determining a first change feature of popularity and a first vaccination result based on extracted sample change features of popularity corresponding to the first training data, and determining a second change feature of popularity and a second vaccination result based on extracted sample change features of popularity corresponding to the second training data;

for each group of the plurality of groups of training samples, outputting a predicted difference of vaccination result in the historical time period by determining a similarity of vaccination results through processing the first vaccination result and the second vaccination result based on the initial similarity model, thereby obtaining a plurality of predicted differences of vaccination results for the plurality of groups;

generating a trained similarity model by updating parameters of the initial similarity model based on differences between the labels and the plurality of predicted differences of vaccination results; and generating a trained feature model by extracting parameters of any one of the first initial feature model and the second initial feature model and migrating the parameters of any one of the first initial feature model and the second initial feature model to the initial feature model;

determining a prediction result by inputting the information related to the vaccine service within the service scope and the change feature of popularity for the each vaccination point into a prediction model, the prediction result including a number of possible to-be-vaccinated persons at the each vaccination point at the each preset time point; wherein the prediction model is a machine learning model;

determining an allocation scheme for the vaccines based on the prediction result; and transmitting the allocation scheme to the vaccination point terminal.

6. The system of claim 5, wherein the vaccine management platform is configured to perform operations further comprising:

in response to a user query for vaccination information at the each vaccination point through the user platform, sending a vaccination arrangement to the user platform through the vaccine service platform for displaying the vaccination information to a user.

7. The system of claim 5, wherein the change feature of popularity for the each vaccination point is dynamically changed based on change factors, the change factors at least including the epidemic situation and spread degree at the each vaccination point.

8. The system of claim 5, wherein the vaccine management platform is further configured to perform the operations further comprising:

generating the allocation scheme for the each vaccination point by determining, based on the prediction result, a number of vaccines allocated to the each vaccination point and vaccination time; and generating a vaccination arrangement based on the allocation scheme.

* * * * *